United States Patent
Hsu et al.

(10) Patent No.: US 11,800,857 B2
(45) Date of Patent: Oct. 31, 2023

(54) LIVER LESION-MOUSE MODEL

(71) Applicant: KAOHSIUNG MEDICAL UNIVERSITY, Kaohsiung (TW)

(72) Inventors: Shih-Hsien Hsu, Kaohsiung (TW); Li-Ting Wang, Kaohsiung (TW); Shen-Nien Wang, Kaohsiung (TW); Kwei-Yan Liu, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 514 days.

(21) Appl. No.: 16/590,392

(22) Filed: Oct. 2, 2019

(65) Prior Publication Data

US 2021/0100226 A1    Apr. 8, 2021

(51) Int. Cl.
*A01K 67/027* (2006.01)
*C12N 15/85* (2006.01)
*C12N 5/071* (2010.01)

(52) U.S. Cl.
CPC ...... *A01K 67/0276* (2013.01); *A01K 67/0271* (2013.01); *C12N 15/8509* (2013.01); *A01K 2227/105* (2013.01); *A01K 2267/03* (2013.01); *C12N 5/067* (2013.01); *C12N 2015/8527* (2013.01)

(58) Field of Classification Search
None
See application file for complete search history.

(56) References Cited

PUBLICATIONS

Hsu et al Cancer Res; 73(2); 508-18 (Year: 2013).*
Zeng et al Gastroenterology, 154(6) sup. 1, S-1160 Abstracts#S1504 (Year: 2018).*
Krstic et al Int. J. Mol. Sci. 19, 921, 1-23 (Year: 2018).*
Wang et al Journal of Molecular Cell Biology, 5, 147-150 (Year: 2013).*
Katz et al Gasteroenterology, 142, 1229-1239 (Year: 2012).*
Wang et al Oncotarget, 24, 36924-36939 (Year: 2017).*
Seino et al The journal of Biol. Chemistry, 283 (8), 4905-4911 (Year: 2008).*
Lau et al., J Pathol 241: 36-44 (Year: 2017).*
Hsu et al Cancer Res; 73(2); 508-18. (Year: 2012).*
Zhang et al Archives of Toxicology 92:2885-2896 (Year: 2018).*
Hsu et al Molecular Carcinogenesis.;56:2167-2177. (Year: 2017).*
Jennie Ka Ching Lau et al., Animal models of non-alcoholic fatty liver disease: current perspectives and recent advances, J Pathol 2017; 241: 36-44. DOI: 10.1002/path.4829.
Takuma Tsuchida et al., A Simple Diet- and Chemical-Induced Murine NASH Model with Rapid Progression of Steatohepatitis, Fibrosis and Liver Cancer, J Hepatol. Aug. 2018 ; 69(2): 385-395. doi:10.1016/j.jhep.2018.03.011.

* cited by examiner

*Primary Examiner* — Anoop K Singh
(74) *Attorney, Agent, or Firm* — Hannah Tien

(57) ABSTRACT

A liver lesion-mouse model which is a liver-specific ISX gene expression and p53 gene knockout transgenic mouse, wherein liver lesion develops after the mouse is fed with a high calorie diet.

1 Claim, 6 Drawing Sheets
(3 of 6 Drawing Sheet(s) Filed in Color)

Figure 3A
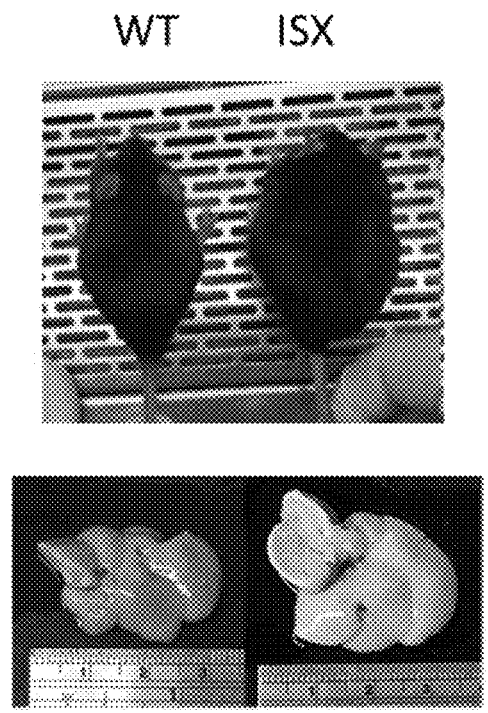
Figure 3B
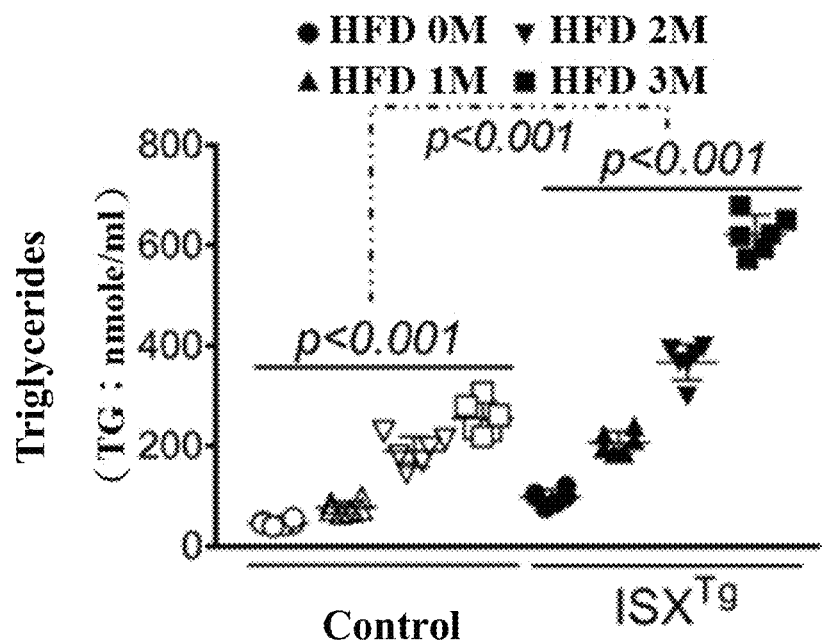
Figure 3

Figure 6A
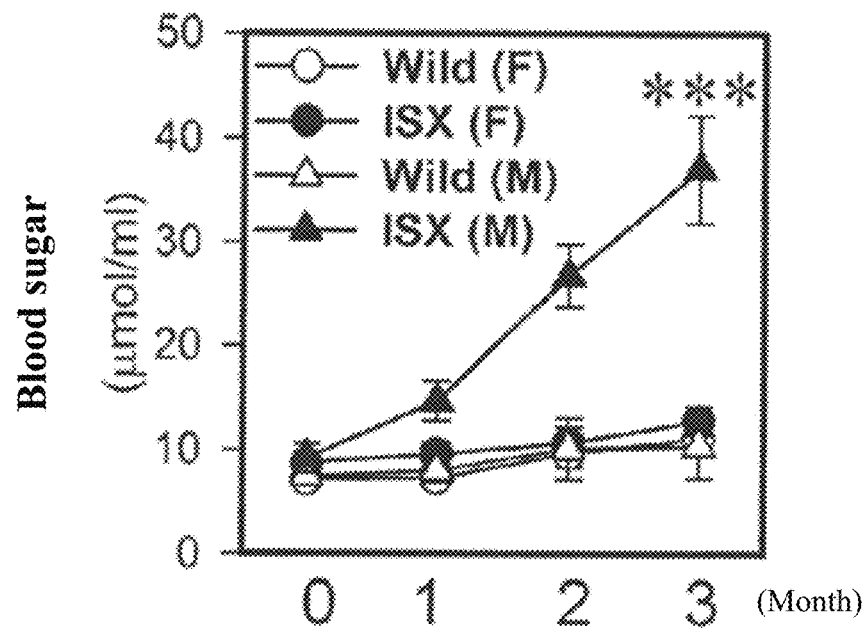
Figure 6B
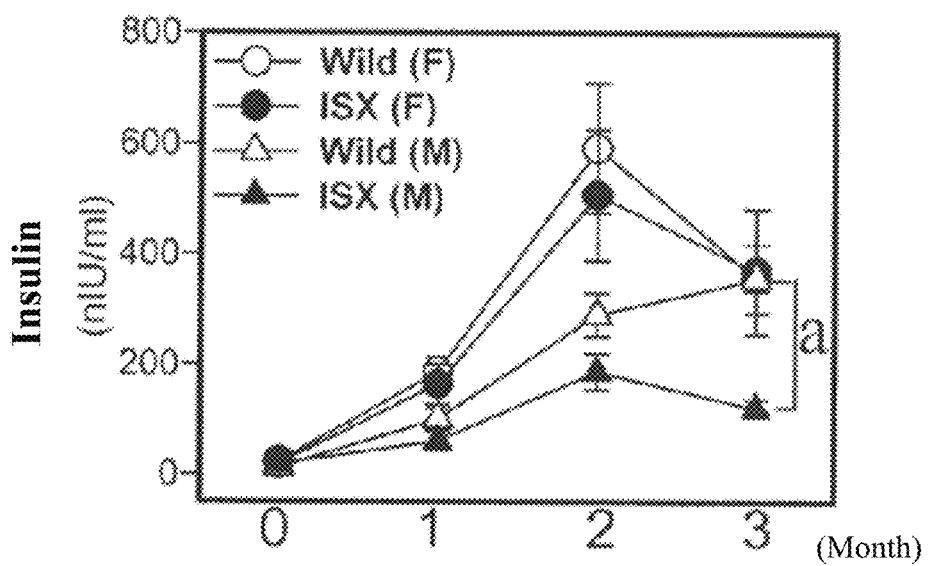
Figure 6

LIVER LESION-MOUSE MODEL

FIELD OF THE INVENTION

The present invention relates to a liver lesion-mouse model, in particular the liver of the mouse specifically expresses ISX gene and p53 gene is knocked out specifically in the liver, so that liver lesion can be induced after the mouse is fed with a high calorie diet.

BACKGROUND OF THE INVENTION

Hepatocellular carcinoma (HCC) is the fifth most common malignancy and the third leading cause of death because late diagnosis. The major risk factors for HCC are virus infection (e.g. HBV or HCV), environment, diet, pollutants and drug use in Taiwan, but fat accumulation in liver induced by high calories diet in Europe and USA. Until now, no effective treatment is adapted for HCC beyond early diagnosis and surgical operation. In recent years, due to the westernization of dietary intake in Taiwan gradually, fatty liver (Steatosis) has gradually become a major cause of chronic metabolic diseases and liver cancer (HCC). Non-alcoholic fatty liver disease (NAFLD) is a common chronic liver disease that ranges from accumulation of fat drop in the liver to cirrhosis, a chronic liver fibrosis disease that often leads to HCC. Although intake of high calorie diet, obesity, metabolic disorders, and a variety of inflammatory reactions are considered factors that promote the development of the disease, the pathogenic mechanism of this chronic liver disease and liver cancer caused by NAFLD remains largely unknown, and no relevant biomarkers is available.

Homeobox gene-ISX (ISX) is a homeobox gene specifically expressed in the intestine. It is a transcription factor induced by pro-inflammatory cytokines (IL-6) and highly expressed in hepatoma cells and HCC patients' tissues. In the nucleus, through directly binding to promotors of downstream cell cycle regulators (cyclin D1 and E2F2), ISX regulates the expression of downstream genes related to the cell cycle, and regulates proliferation of cancer cells and shows high correlation to patient survival time, tumor size and progression stage. In addition, the exposure to environmental pollutants will also trigger and exacerbate liver cancer by inducing the expression of ISX homeobox gene and relevant epigenetic genes via the function of its upstream regulatory gene-AHR. At the same time, the expression of ISX in HCC cells can also inhibit the host's own immune system through the regulation of immune checkpoint and tryptophan metabolism related genes to promote the further growth and metastasis of hepatoma cells.

Therefore, for purpose of research and treatment of liver diseases, it is necessary to establish a liver disease-animal model.

SUMMARY OF THE INVENTION

The present invention relates to a liver lesion-mouse model which is a liver-specific ISX gene expression and p53 gene knockout transgenic mouse, wherein liver lesion develops after the mouse is fed with a high calorie diet.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 is an analysis of body weight and different physical parameters of the blood of the mice collected at different points in time while being fed with high fat diet (HFD). FIG. 3A shows that as the HFD feeding period increases (from 0 month (0 M), one month (1 M), two months (2 M) to three months (3 M)), the body weight of the mFgg-ISX/Alb-Cre-p53$^{loxp/loxp}$ mice also increases significantly along with the feeding period, as compared to normal mice of the same birth. The mice also develop fatty liver and the volume of the liver is increased. FIG. 3B shows that triglyceride (TG), a lipid-related metabolite in the blood, also increases significantly with an increased HFD feeding period. Core: gene transgenic mouse of hepatitis C virus core protein (HCV core protein); WT: wild type mouse; ISX: mFgg-ISX/Alb-Cre-p53$^{loxp/loxp}$ mouse; Control: wild type mouse; ISX$^{TG}$: mFgg-ISX/Alb-Cre-p53$^{loxp/loxp}$ mouse.

FIG. 6 shows the analysis of different physiological parameters of the blood of the mice collected at different points in time during high a fat diet (HFD) feeding period. FIG. 6A shows that when the HFD feeding period is increased, the blood sugar of the mFgg-ISX/Alb-Cre-p53$^{loxp/loxp}$ mice changes abnormally as compared with normal mice of the same birth.

FIG. 6B shows that when the HFD feeding period is increased, insulin in the mFgg-ISX/Alb-Cre-p53$^{loxp/loxp}$ mice changes abnormally as compared to normal mice of the same birth. Wild: wild type mice; ISX: mFgg-ISX/Alb-Cre-p53$^{loxp/loxp}$ mice; F: Female; M: Male.

DETAILED DESCRIPTION OF THE INVENTION

Figure 1:
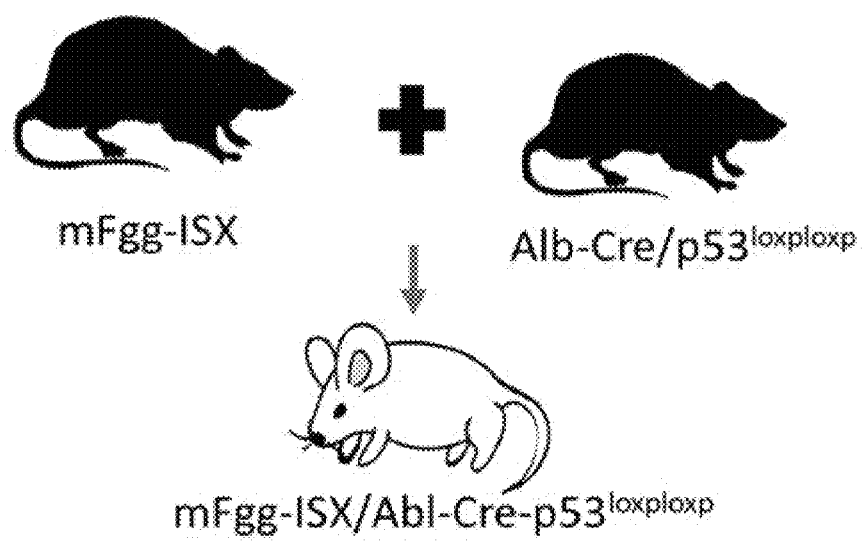
FIG. 1 is a mating process for producing a mFgg-ISX/Alb-Cre-p53$^{loxp/loxp}$ mouse.

The present invention utilizes a mFgg-ISX mouse to mate with an Alb-Cre-p53$^{loxp/loxp}$ mouse to produce a progeny of mFgg-ISX/Alb-Cre-p53$^{loxp/loxp}$ mouse. The mFgg-ISX/Alb-Cre-p53$^{loxp/loxp}$ mouse is a liver-specific ISX gene expression and p53 gene knockout transgenic mouse. It is discovered by experiments that fatty liver can be rapidly induced in the mouse body of the mFgg-ISX/Alb-Cre-p53$^{loxp/loxp}$ mouse by intake of a high calorie diet, then chronic liver fibrosis, and finally develops into liver diseases such as liver cancer. In addition, while liver disease is developing in the mouse, metabolic diseases similar to human liver diseases also develop.

Therefore, the mFgg-ISX/Alb-Cre-p53$^{loxp/loxp}$ mouse is an animal model in which fatty liver, chronic liver diseases and liver cancer are induced through intake of a high-calorie diet.

The term "a" or "an" as used herein is to describe elements and ingredients of the present invention. This term is only for convenience of description and the basic idea of the present invention. The description should be understood as comprising one or at least one, and unless otherwise explicitly indicated by the context, singular terms include pluralities and plural terms include the singular. When used in conjunction with the word "comprising" in a claim, the term "a" or "an" may mean one or more than one.

The present invention provides a method for producing a liver lesion-mouse model, steps of which include: (a) transfecting mouse embryos with ISX gene driven by a liver-specific promoter by micro-injection into a mother mouse of the same strain to develop into adult mice; (b) screening positive transgenic mice with ISX gene from the adult mice obtained in step (a) by analysis of a genetic testing method to obtain a liver-specific ISX gene transgenic mouse; and (c) mating the liver-specific ISX gene transgenic mouse and a liver-specific p53 gene knockout mouse to obtain a liver-specific ISX gene expression and p53 gene knockout transgenic mouse.

As used herein, "liver lesion" refers to liver lesion caused by liver cells injured or damaged due to certain factors, which may further lead to effects on liver functions. In general, many liver diseases may develop during the development of the liver lesion, for example, metabolic abnormal liver diseases, chronic liver diseases, fatty liver, liver fibrosis, cirrhosis, and liver cancer. Therefore, the liver lesion-mouse model of the present invention is a mouse model of diseases related to the development of liver lesion, and can be used to study the diseases related to the development of liver lesion, for example a mechanism for converting fatty liver into liver fibrosis or liver cancer. As a result, in one embodiment, the diseases related to the development of liver lesion include metabolic abnormal liver diseases, chronic liver diseases, fatty liver, liver fibrosis, cirrhosis, and liver cancer.

In one embodiment, the liver lesion is liver lesion induced by a high calorie diet. Fat accumulation can be caused in the liver of the liver-specific ISX gene expression and p53 gene knockout transgenic mouse of the present invention after the transgenic mouse is fed with a high calorie diet, which further causes liver lesion. Accordingly, intake of a high calorie diet induces liver diseases such as fatty liver, liver fibrosis, even develops into liver cancer in the transgenic mouse. Therefore, after the transgenic mouse is fed with a high calorie diet, the development of liver lesion in the transgenic mouse is induced. In a preferred embodiment, the liver lesion-mouse model is a liver lesion-mouse model induced by a high calorie diet. In a more preferred embodiment, the liver lesion-mouse model is a mouse model of diseases related to the development of liver lesion induced by a high calorie diet.

In another embodiment, the high calorie diet comprises a high fat diet, a high carbohydrate diet, a high fat high carbohydrate diet, or a high cholesterol diet. In a preferred embodiment, the high calorie diet is a high fat diet. In another embodiment, the fat of the high fat diet, the carbohydrate of the high carbohydrate diet, or the fat and carbohydrate of the high fat high carbohydrate diet account for 40-80% of the total calories. In a preferred embodiment, the fat of the high fat diet, the carbohydrate of the high carbohydrate diet, or the fat and carbohydrate of the high fat high carbohydrate diet account for 60-80% of the total calories.

As used herein, "liver-specific ISX gene transgenic mouse" refers to a mouse in which ISX gene expresses specifically in the liver. Since the front end of the ISX gene of the mouse is integrated with a fragment of liver-specific promoter, the ISX gene is expressed specifically on the liver. In one embodiment, the liver-specific promoter comprises mFgg and Alb. In a preferred embodiment, the liver-specific promoter is mFgg. Thus, in another embodiment, the liver-specific ISX gene transgenic mouse is a transgenic mouse with liver-specific ISX gene driven by mFgg; or is refer to as a mFgg-ISX mouse.

Step (b) of the method for producing a liver lesion-mouse model of the present invention further comprises step (b1), which precedes step (c), comprising mating the liver-specific ISX gene transgenic mouse with a wild type mouse of the same strain to generate F0 mice, and then screening positive F0 mice with ISX gene from the F0 mice by using a genetic testing method to obtain a liver-specific ISX gene transgenic F0 mouse. The purpose of step (b1) is to ensure that the characteristics of the liver-specific ISX gene transgenic mouse (i.e., the ISX gene expresses specifically in the liver) are inherited by the next generation (e.g., the F0 mice).

Therefore, either the positive mice with ISX gene in step (b) or the positive F0 mice with ISX gene in step (b1) can be further analyzed by a genetic testing method to confirm that ISX gene expresses specifically in the liver, thereby confirming that they all are liver-specific ISX gene transgenic mice. Therefore, the liver-specific ISX gene transgenic mice before step (c) can be replaced with the liver-specific ISX gene transgenic F0 mice, because when the liver-specific ISX gene transgenic F0 mice and the liver-specific p53 gene knockout mice are mated, the liver-specific ISX gene expression and p53 gene knockout transgenic mouse can also be obtained.

As used herein, a "liver-specific p53 gene knockout mouse" refers to a mouse with p53 gene specifically knocked out in the liver. The liver-specific p53 gene knockout mouse can be obtained through activating Cre enzyme by a liver-specific promoter to specifically cleave the p53 gene sequence having loxp sites to delete the genes flanked by these two loxP sites, including the p53 gene which is located between the two loxp sites, thereby achieving the goal of specifically knocking out p53 gene in the liver. In one embodiment, the liver-specific promoter comprises mFgg and Alb. In a preferred embodiment, the liver-specific promoter is Alb. In another embodiment, the liver-specific p53 gene knockout mouse is a mouse with liver-specific knock-out p53 gene driven by Alb; or is referred to as an Alb-Cre-p53$^{loxp/loxp}$ mouse.

Therefore, the method for producing the liver-specific p53 gene knockout mouse is as follows: mating an Alb-Cre gene transgenic mouse with a p53$^{loxp/loxp}$ gene transgenic mouse to generate an Alb-Cre-p53$^{loxp/loxp}$ p53 homozygous gene transgenic mouse, i.e., the liver-specific p53 gene knockout mouse.

Steps for producing an Alb-Cre gene transgenic mouse comprise: (e) transfecting mouse embryos with Alb-Cre gene by micro-injection into a mother mouse of the same strain to develop into adult mice; and (f) screening positive mice with Alb gene from the adult mice obtained in step (e) by a genetic testing method to obtain an Alb-Cre gene transgenic mouse. In addition, step (f) further comprises step (f1) which comprises mating the Alb-Cre gene transgenic mouse with a wild type mouse of the same strain to generate F0 mice, then screening a positive F0 mouse with Alb gene from the F0 mice by using a genetic testing method to obtain an Alb-Cre gene transgenic F0 mouse. The purpose of step (f1) is to ensure that the characteristics of the Alb-Cre gene-transgenic mouse (i.e., Alb gene expresses specifically in the liver) are inherited by the next generation (e.g., F0 mice).

Therefore, either the positive mice with Alb gene in step (f) or the positive F0 mice with Alb gene in step (f1) can be further analyzed by a genetic testing method to confirm that Alb gene expresses specifically in the liver, thereby confirming that they all are Alb-Cre gene-transgenic mice.

The steps of the method for producing a $p53^{loxp/loxp}$ gene transgenic mouse comprise: (g) transfecting mouse embryos in which p53 gene having loxp sequences into a mother mouse of the same strain to develop into adult mice; and (h) screening a positive mouse with $p53^{loxp/loxp}$ gene from the adult mice produced in step (g) by analysis of a genetic testing method to obtain a $p53^{loxp/loxp}$ gene transgenic mouse. In addition, step (h) further comprises step (h1) which comprises mating the $p53^{loxp/loxp}$ gene transgenic mouse and a mouse of the same strain to generate F0 mice, and screening a positive F0 mouse with $p53^{loxP/loxP}$ gene from the F0 mice by a genetic testing method to obtain a $p53^{loxP/loxP}$ gene transgenic F0 mouse. The purpose of (f1) step is to ensure that the characteristics of the $p53^{loxp/loxp}$ gene transgenic mouse are inherited by the next generation (e.g., F0 mice).

Therefore, either the positive mice with $p53^{loxp/loxp}$ gene of step (h) or the positive F0 mice with $p53^{loxP/loxP}$ gene of step (f1) can be further analyzed by a genetic testing method to confirm that they all are $p53^{loxp/loxp}$ gene transgenic mice.

In one embodiment, the genetic testing method comprises PCR and RT-PCR.

After the liver-specific ISX gene transgenic mouse and the liver-specific p53 gene knockout mouse are mated, the liver-specific ISX gene expression and p53 gene knockout transgenic mouse is produced. The liver of the liver-specific ISX gene expression and p53 gene knockout transgenic mouse specifically expresses ISX gene, but p53 gene is absent; thus, the transgenic mouse, after being fed with a high calorie diet, shows liver diseases, such as fatty liver, liver fibrosis, and even liver cancer. Therefore, the liver-specific ISX gene expression and p53 gene knockout transgenic mice can be used to study the development of liver lesions or liver diseases caused by a high calorie diet, including metabolic abnormal liver diseases, chronic liver diseases, fatty liver, liver fibrosis, cirrhosis and liver cancer.

In one embodiment, the strain of the transgenic mouse comprises C57BL/6, Balb/c, and FVB/N.

The present invention also provides a method for screening drugs for treating liver lesion, which comprises the following steps of (1) providing a liver-specific ISX gene expression and p53 gene knockout transgenic mouse suffering from liver lesion, wherein the liver-specific ISX gene expression and p53 gene knockout transgenic mouse is produced by mating a liver-specific ISX gene transgenic mouse and a liver-specific p53 gene knockout mouse, and symptoms of liver lesion develop after the liver-specific ISX gene expression and p53 gene knockout transgenic mouse is fed with a high calorie diet; (2) administering a candidate drug to the liver-specific ISX gene expression and p53 gene knockout transgenic mouse of step (1); and (3) observing and analyzing treatment conditions of the liver lesion of the liver-specific ISX gene expression and p53 gene knockout transgenic mouse by the candidate drug, determining that the candidate drug is a drug capable of treating the liver lesion when the liver lesion of the liver-specific ISX expression and p53 gene knockout transgenic mice is effectively improved.

In one embodiment, the liver lesion comprises a disease related to the development of liver lesion. In a preferred embodiment, the disease related to the development of liver lesion comprises metabolic abnormal liver diseases, chronic liver diseases, fatty liver, liver fibrosis, cirrhosis, and liver cancer.

In one embodiment, the liver lesion is a liver lesion induced by a high calorie diet. In a preferred embodiment, the liver lesion comprises a disease related to the development of liver lesion induced by a high calorie diet.

In one embodiment, the high calorie diet comprises a high fat diet, a high carbohydrate diet, a high fat high carbohydrate diet, or a high cholesterol diet. In a preferred embodiment, the high calorie diet is a high fat diet. In another embodiment, the fat of the high fat diet, the carbohydrate of the high carbohydrate diet, or the fat and the carbohydrate of the high fat high carbohydrate diet account for 40-80% of the total calories. In a preferred embodiment, the fat of the high fat diet, the carbohydrate of the high carbohydrate diet, or the fat and the carbohydrate of the high fat high carbohydrate diet account for 60-80% of the total calories.

In addition, symptoms of fatty liver develop in the liver-specific ISX gene expression and p53 gene knockout transgenic mouse after the mouse is fed with the high calorie diet for 1 month, and symptoms such as severe fatty liver and liver fibrosis develop after the mouse is fed for 2 months, and severe liver fibrosis and even liver cancer develops after the mouse is fed for 3 months. Therefore, various liver diseases develop in the liver-specific ISX gene expression and p53 gene knockout transgenic mouse after the mouse is fed with a high calorie diet for 1 month, allowing researchers to test various drugs for treating liver diseases, for example, drugs for treating fatty liver or drugs for treat cancer.

In one embodiment, the liver-specific ISX gene transgenic mouse is a transgenic mouse with liver-specific ISX gene driven by a liver-specific promoter. In a preferred embodiment, the liver-specific promoter comprises mFgg and Alb. In a more preferred embodiment, the liver-specific promoter is mFgg. Therefore, the liver-specific ISX gene transgenic mouse is a transgenic mouse with liver-specific ISX gene driven by mFgg.

In another embodiment, the liver-specific p53 gene knockout mouse is a mouse with liver-specific p53 gene knockout driven by a liver-specific promoter. In a preferred embodiment, the liver-specific promoter comprises mFgg and Alb. In a more preferred embodiment, the liver-specific promoter is Alb. Therefore, the liver-specific p53 gene knockout mouse is a mouse with liver-specific p53 gene knockout driven by Alb.

In one embodiment, the strain of the liver-specific ISX gene expression and p53 gene knockout transgenic mouse comprises C57BL/6, Balb/c, and FVB/N.

In conventional treatment methods in the related field of the present invention, the candidate drug is administered to the liver-specific ISX gene expression and p53 gene knockout transgenic mouse through a number of different routes. In some embodiments, the administration route of the candidate drug comprises external, intravenous, intramuscular, subcutaneous, topical, oral inhalation or peritoneal administration. The candidate drug is delivered to a target site through the digestive and circulatory system.

As used herein, the term "treating" refers to alleviating symptoms or complications; delaying the progression of a disease, a disorder or a medical condition; alleviating or ameliorating symptoms and complications; and/or curing or eliminating a disease, a disorder or a medical condition.

The present invention further provides a liver lesion-mouse model which comprises: a liver-specific ISX gene expression and p53 gene knockout transgenic mouse, wherein liver lesion develops in the liver-specific ISX gene expression and p53 gene knockout transgenic mouse develops liver lesions after the mouse is fed with a high calorie diet.

In one embodiment, the liver lesion comprises a disease related to the development of liver lesions. In a preferred embodiment, the disease related to the development of liver lesions comprises metabolic abnormal liver diseases, chronic liver diseases, fatty liver, liver fibrosis, cirrhosis, and liver cancer.

In another embodiment, the liver lesion is liver lesion induced by a high calorie diet. In a preferred embodiment, the liver lesion comprises a disease related to the development of liver lesions induced by a high calorie diet.

The liver-specific ISX gene expression and p53 gene knockout transgenic mouse begins to be fed with a high fat diet upon reaching adult stage, fatty liver develops after the mouse is fed for 1 month, diseases such as liver fibrosis, a metabolic abnormal liver disease and a chronic liver disease develop after 2 months, and even liver cancer develops after 3 months. In one embodiment, the liver-specific ISX gene expression and p53 gene knockout transgenic mouse is fed with a high calorie diet for at least one month. In a preferred embodiment, the liver-specific ISX gene expression and p53 gene knockout transgenic mouse is fed with a high calorie diet for at least two months. In a more preferred embodiment, the liver-specific ISX gene expression and p53 gene knockout transgenic mouse is fed with a high calorie diet for at least 3 months.

In addition, after the liver-specific ISX gene expression and p53 gene knockout transgenic mouse is fed with a high calorie diet for 2 months, the blood sugar of the blood increases abnormally, and a condition of insulin resistance is also observed.

In one embodiment, the high calorie diet comprises a high fat diet, a high carbohydrate diet, a high fat high carbohydrate diet, or a high cholesterol diet. In a preferred embodiment, the high calorie diet is a high fat diet.

In another embodiment, the liver-specific ISX gene expression and p53 gene knockout transgenic mouse is obtained by mating a liver-specific ISX gene transgenic mouse with a liver-specific p53 gene knockout mouse.

The advantage of the liver-specific ISX gene expression and p53 gene knockout transgenic mouse is that, currently 17 weeks or more are required to develop fatty liver in a fatty acid-mouse model induced by a high fat diet, however symptoms of fatty liver develop in the liver-specific ISX gene expression and p53 gene knockout transgenic mouse after the mouse is fed with a high fat diet for 1 month (approximately 4 weeks); therefore, the present invention can significantly reduce the time required to induce fatty liver in a mouse by a high fat diet. In addition, intake of a high calorie diet can quickly induce the development of a liver disease such as fatty liver, chronic fibrosis and even liver cancer in the liver-specific ISX gene expression and p53 gene knockout transgenic mouse; and during the development of the liver disease in the transgenic mouse, metabolic diseases similar to human liver diseases also develop. Therefore, the mouse model of the present invention can be used for multiple purposes, for example, exploring mechanisms of liver cancer caused by fatty liver, discovering early biological factors of liver diseases and developing animal models for drug treatment related to liver diseases, and providing possible new treatments and the impact of high calorie diet on the development of liver diseases.

EXAMPLES

The examples below are non-limiting and are merely representative of various aspects and features of the present invention.

Method:

(1) Method for Producing mFgg-ISX/Alb-Cre-p53$^{loxp/loxp}$ Mice

Liver-specific ISX gene transgenic mice were obtained from the National Laboratory Animal Center (Taipei, Taiwan). The method for producing the liver-specific ISX gene transgenic mouse included: transfecting mouse embryos with ISX gene driven by a mFgg promoter (a liver-specific promoter) by micro-injection into a mother mouse of the same strain to develop into adult mice; and (2) screening positive mice with ISX gene from the adult mice by PCR analysis to obtain the liver-specific ISX gene transgenic mice. Alternatively, the positive mice with ISX gene mated with the wild type mice of the same strain to generate F0 mice, and the PCR method was utilized to screen positive F0 mice with ISX gene, the liver-specific ISX gene transgenic mice were also obtained. The liver-specific ISX gene transgenic mice obtained above could be reanalyzed by RT-PCR to confirm that the liver of the liver-specific ISX gene transgenic mouse specifically expressed the ISX gene. The liver-specific ISX gene transgenic mice (mFgg-ISX mice) were hybridized with the liver-specific p53 gene knockout male mice (p53$^{loxP/-}$; Albcre) (Alb-Cre-p53$^{loxp/loxp}$ mice) to generate the desired Genotype. Genotyping techniques were used to confirm that the transgenic mice used for experiments had the desired genotype.

In addition, the method for producing the liver-specific p53 gene knockout mouse was to mate an Alb-Cre mouse with a p53$^{loxp/loxp}$ mouse to generate an Alb-Cre/p53$^{loxp/loxp}$ p53 gene homozygous mouse, i.e., a liver-specific p53 knockout mouse.

The preparation method of the Alb-Cre mouse was: (1) transfecting mouse embryos with Alb-Cre gene by micro-injection into a mother mouse of the same strain to develop into adult mice; and (2) screening positive mice with Alb gene by PCR analysis from the adult mice to obtain Alb-Cre mice. Alternatively, the positive mice with Alb gene mated with homozygous mice of the same strain to generate F0 mice, and positive Alb gene transgenic mice, i.e., Alb-Cre mice, were screen from the F0 mice by PCR. The expression of Alb gene in the liver of the Alb-Cre mice obtained above was confirmed by RT-PCR analysis.

The preparation method of p53$^{loxp/loxp}$ mice: (1) transfecting mouse embryos in which p53 gene having loxp sequences into a mother mouse of the same strain to develop into adult mice; and (2) screening mice with the genes of p53$^{loxp/loxp}$ by PCR analysis to obtain p53$^{loxp/loxp}$ homozygous transgenic mice. Alternatively, the p53$^{loxp/loxp}$ mice mated with mice of the same strain to generate F0 mice, and transgenic mice with p53$^{loxp/loxp}$ gene were screened from the F0 mice by PCR, i.e., p53$^{loxp/loxp}$ mice. The p53$^{loxp/loxp}$ mice obtained above were reanalyzed and confirmed by RT-PCR.

(2) Analysis of Triglycerides

The experiments of the present invention were carried out by using an enzyme-linked immunosorbent assay (ELISA) kit for analysing mouse triglyceride (TG) purchased from the BioVision Inc. in accordance with the manufacturer's instructions. Serum was obtained from the heart of a mouse, a supernatant was obtained after centrifugation, and then the supernatant was subjected to three repeated ELISA assays. In the present invention, the triglyceride concentration was calculated by referring to a standard curve of purified triglyceride provided in the ELISA kit.

(3) Hematoxylin and Eosin Stain

Slides were dewaxed, the slides were immersed in xylene twice, 10 minutes each time; then immersed in absolute alcohol twice for re-hydration, 5 minutes each time; then immersed in 95% alcohol for 2 minutes, and immersed in 70% alcohol for 2 minutes. The slides were briefly washed with distilled water, stained in Harris hematoxylin solution for 8 minutes, washed for 5 minutes under running tap water, excess staining was removed in 1% acidic alcohol for 30 seconds, rinsed with tap water for 1 minute, turned blue in 0.2% ammonia water or saturated lithium carbonate solution for 30 seconds to 1 minute, washed for 5 minutes under running tap water, rinsed with 95% alcohol, and immersed for 10 times. The slides were counterstained by reacting in an eosin solution for 30 seconds to 1 minute, dehydrated with 95% alcohol, and immersed in absolute alcohol twice, 5 minutes each time, washed by immersing in xylene twice, 5 minutes each time, and an embedding solution containing xylene was used for embedding.

(4) Oil Red O Staining

Fresh frozen tissue slices of 5-10 μM thickness were cut and embedded on glass slides. The slides were air dried at room temperature for 30-60 minutes, and then fixed in ice-cold 10% formalin for 5-10 minutes. Dried again with air for 30-60 minutes or rinsed immediately with distilled water for 3 times. The slides were allowed to be air dried for a few minutes. The slides were placed in absolute propylene glycol for 2-5 minutes to prevent water from being brought into the oil red 0, stained in a preheated Oil Red 0 solution for 8-10 minutes in an oven at 60° C., placed in 85% propylene glycol solution for 2-5 minutes to remove excessive staining. Rinsed twice with distilled water. Stained for 30 seconds in Gill or Mayer's hematoxylin. Washed thoroughly under running tap water for 3 minutes. The slides were placed in distilled water, and embedded with glycerin jelly or other embedding solutions.

(5) Statistics:

Quantitative results of the present invention were expressed as mean±standard deviation, and statistically significant differences were expressed using the student's t test. Variations between different groups were determined by chi-squared analysis, one-way analysis of variance (ANOVA) and Fisher's exact analysis, $p<0.05$.

Figure 2:
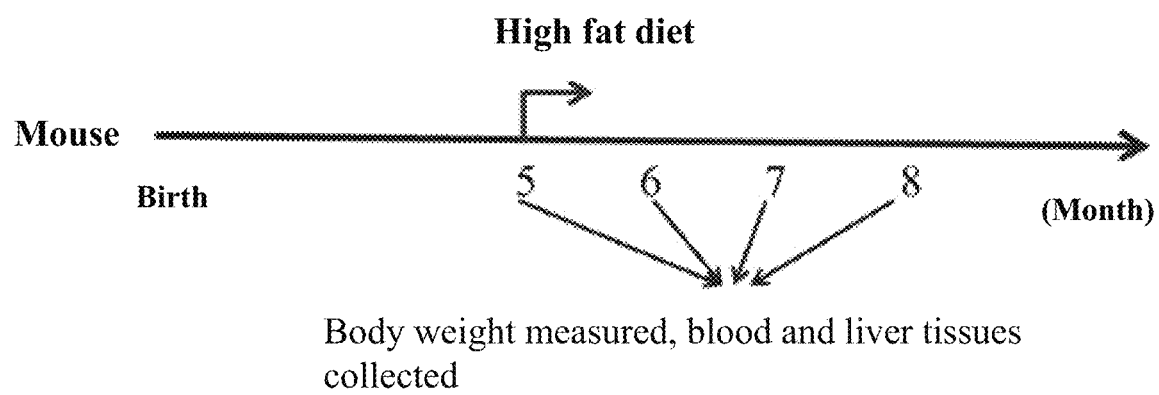
FIG. 2 is the timeline for inducing fatty liver and liver cancer in a mFgg-ISX/Alb-Cre-p53$^{loxp/loxp}$ mouse.

Results:

mFgg-ISX mice were mated with Alb-Cre-p53$^{loxp/loxp}$ mice to generate mFgg-ISX/Alb-Cre-p53$^{loxp/loxp}$ mice (FIG. 1), followed by a 60% high fat diet (HFD) when the mFgg-ISX/Alb-Cre-p53$^{loxp/loxp}$ mice grew to 5 months old, the mice were sacrificed one month, two months and three months after being fed with the high fat diet, respectively, body weight was measured, blood was taken, and the liver tissues of the mice were removed when the mice were sacrificed. FIG. 2 is a timeline of the experiment conducted in the present invention.

Body weight and different physiological parameters of the blood of the mice collected at different points in time while the mice were fed with a high fat diet (HFD) were analyzed. It was found that when the HFD feeding period was increased, the body weight of the ISX gene transgenic mice increased significantly as compared to that of normal mice of the same birth (FIG. 3A). Also, triglyceride (TG), a lipid-related metabolite in blood, also increased significantly when the HFD feeding period was increased (FIG. 3B).

Figure 4:
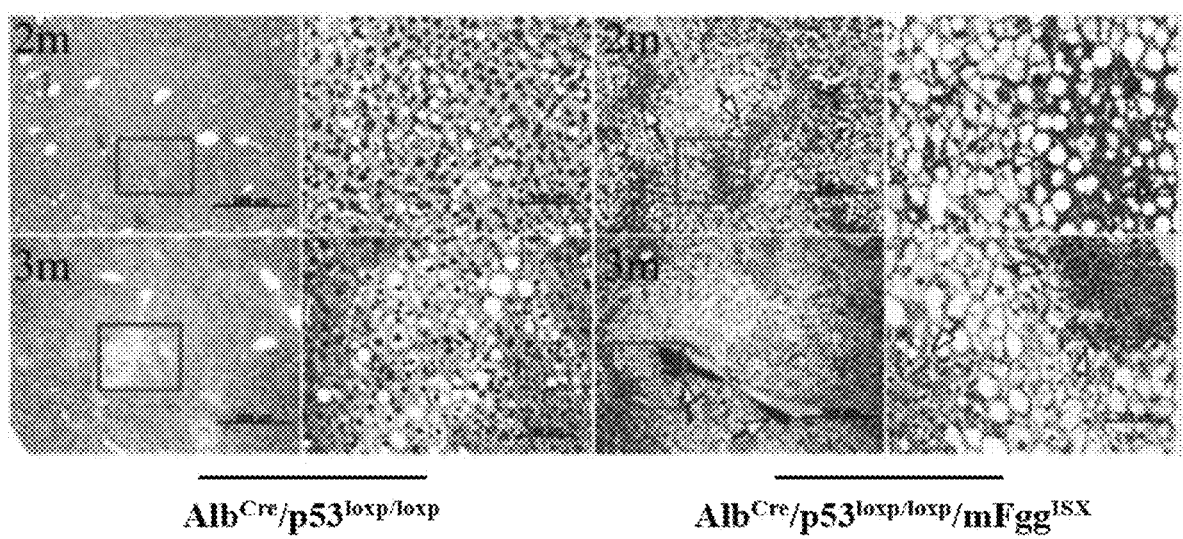
FIG. 4 shows that the mFgg-ISX/Alb-Cre-p53$^{loxp/loxp}$ mice have severe fatty liver in the liver 2 months after being fed with a high fat diet (HFD), and an initial phase of fibrosis also develops. In the third month of the HFD feeding period, in addition to severe liver fibrosis, liver cancer also develops in the liver. 2 m: 2 months; 3 m: 3 months. Alb$^{cre}$/p53$^{loxp/loxp}$; Alb-Cre-p53$^{loxp/loxp}$; mice; Alb$^{cre}$/p53$^{loxP/loxp}$/mFgg$^{ISX}$; mFgg-ISX/Alb-Cre-p53$^{loxp/loxp}$ mice.
Figure 5:
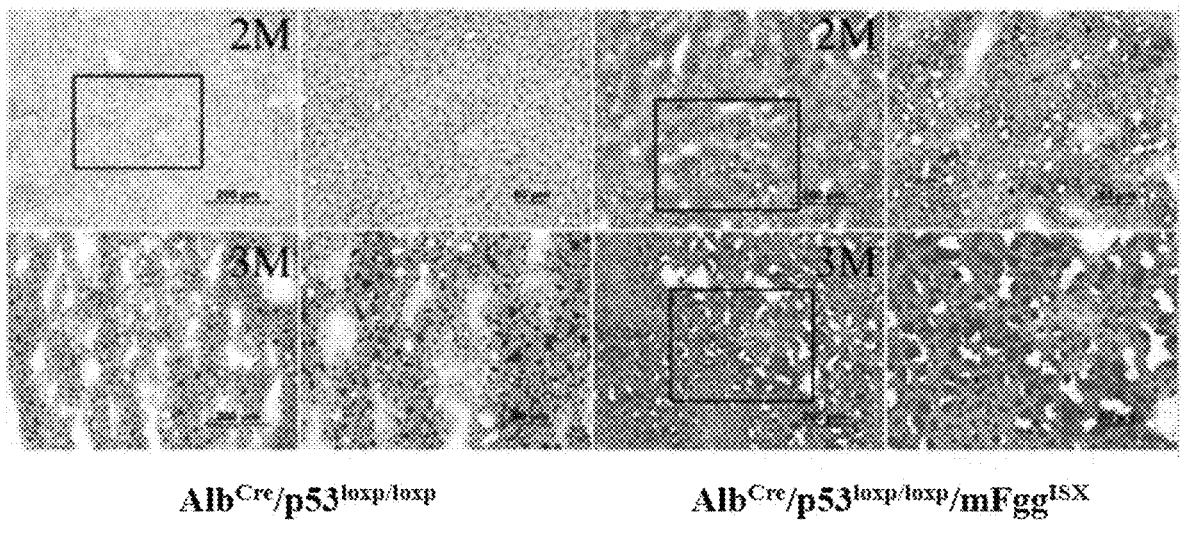
FIG. 5 shows that severe fat accumulation is found in the liver of the mFgg-ISX/Alb-Cre-p53$^{loxp/loxp}$ mice after being fed with a high fat diet for 2 months by using the oil red stain method. 2 M: 2 months; 3 M: 3 months. AlbCre/p53$^{loxp/loxp}$: Alb-Cre-p53$^{loxp/loxp}$ mice; Alb$^{cre}$/p53$^{loxp/loxp}$/mFgg$^{ISX}$; mFgg-ISX/Alb-Cre-p53$^{loxp/loxp}$ mice.

Liver tissues collected from the mice fed with a HFD were stained with hematoxylin and eosin stain (H&E stain), it was found that after the mFgg-ISX/Alb-Cre-p53$^{loxp/loxp}$ mice were fed with the HFD diet for 1 month, obvious fatty liver condition was observed in the liver, after 2 months of the HFD, in addition to severe fatty liver, severe liver fibrosis and cirrhosis also developed in the liver. After 3 months of the HFD diet, in addition to severe liver fibrosis, one third of the mice also developed liver cancer (FIG. 4). Finally, severe fat accumulation was found in the liver of the mFgg-ISX/Alb-Cre-p53$^{loxp/loxp}$ mice after 2 months of the HFD by using the oil red stain (FIG. 5). Blood sugar in the blood increased abnormally; as for insulin, it increased in the first two months and insulin resistance developed at the third month of the HFD (FIG. 6).

Those skilled in the art recognize the foregoing outline as a description of the method for communicating hosted application information. The skilled artisan will recognize that these are illustrative only and that many equivalents are possible.

What is claimed is:

1. A transgenic mouse whose genome comprises
    (i) a liver-specific homozygous deletion of endogenous p53 gene, wherein the deleted p53 is a liver specific conditional knockout of the endogenous p53 gene; and
    (ii) a nucleic acid encoding intestine-specific homeobox transcription factor intestine specific homeobox (ISX) under the control of liver specific mFgg promoter;
    wherein said mouse expresses ISX gene but does not express p53 gene in all the liver cells;
    wherein said mouse exhibits: (a) a fatty liver following continuous feeding for one months with a high fat diet (HFD), (b) a liver fibrosis and cirrhosis following continuous feeding for two months with the HFD and (c) a hepatocellular carcinoma (HCC) following continuous feeding for three months with the HFD, wherein fat in said HFD accounts for 40-80% of the total calories.

* * * * *